United States Patent [19]

Kupchik et al.

[11] Patent Number: 4,497,806

[45] Date of Patent: Feb. 5, 1985

[54] TRIORGANOTIN COMPOUNDS, ANTIFUNGAL AND ANTIBACTERIAL COMPOSITIONS CONTAINING SAME, AND METHOD OF USING SAME

[75] Inventors: Eugene J. Kupchik, Howard Beach; Michael A. Pisano, East Norwich, both of N.Y.

[73] Assignee: St. John's University, Jamaica, N.Y.

[21] Appl. No.: 468,727

[22] Filed: Feb. 22, 1983

[51] Int. Cl.³ ................ A61K 31/555; C07D 307/42
[52] U.S. Cl. .................................. 514/189; 549/211
[58] Field of Search ..................... 549/211; 424/245

[56] References Cited

PUBLICATIONS

Kupchik et al., Chem. Abstracts, vol. 96, 217954f, p. 756, 1982.

*Primary Examiner*—Nicky Chan
*Attorney, Agent, or Firm*—Sughrue, Mion, Zinn, Macpeak and Seas

[57] ABSTRACT

Antifungal and antibacterial compounds, compositions containing the same, and method of using the same comprising triorganotin 5-nitro-2-furoates represented by Formula (I)

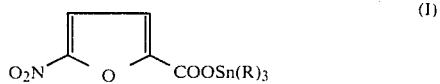

wherein R, which may be the same or different, is an alkyl group, a cycloalkyl group, an aryl group or an aralkyl group, as the active ingredient.

25 Claims, No Drawings

TRIORGANOTIN COMPOUNDS, ANTIFUNGAL AND ANTIBACTERIAL COMPOSITIONS CONTAINING SAME, AND METHOD OF USING SAME

FIELD OF THE INVENTION

The present invention relates to triorganotin 5-nitro-2-furoates, and compositions containing same and method of using same as fungicides and bactericides.

BACKGROUND OF THE INVENTION

Many biocidal applications have been found or suggested for organotin compounds (see J. S. Thayer, *J. Organometal. Chem.*, 76:265 (1974); *Organotin Compounds: New Chemistry and Applications*, J. J. Zuckerman, Ed., American Chemical Society, Washington, D.C., (1976)). Specific organotin compounds currently used in agriculture have been reviewed (see B. Sugavanam, *Tin Its Uses*, 126:4 (1980); F. E. Smith, ibid., 126:6 (1980); S. Haynes, ibid, 127:12(1981)). Their use in agriculture as fungicides and pesticides is of special interest because they degrade into non-toxic inorganic compounds and therefore are not hazardous to the environment (see K. D. Freitag and R. Bock, *Pestic. Sci.*, 5:731 (1974); R. D. Barnes, A. T. Bull, and R. C. Poller, ibid., 4:305 (1973); M. E. Getzendaner and H. B. Corbin, *J. Agr. Food Chem.*, 20:881 (1972); R. Bock and K. D. Freitag, *Naturwissenschaften*, 59:164 (1972); A. J. Chapman and J. W. Price, *Int. Pestic. Control*, 1:11 (1972)).

Recently, a series of diorganotin dihalide complexes have been shown to exhibit anti-tumor activity (see A. J. Crowe and P. J. Smith, *Chem. Ind.* (London), 200 (1980)). In addition, it has been reported that N-substituted N-(triphenylstannyl)cyanamides are better antifungal agents than N-substituted N'-cyano-S-(triphenylstannyl)isothioureas and N-substituted N'-cyano-O-(triphenylstannyl)isoureas (see E. J. Kupchik, M. A. Pisano, A. M. Carroll, J. R. Lumpp, and J. A. Feiccabrino, *J. Pharm. Sci.*, 69:340 (1980)). The N-substituted N-(triphenylstannyl)cyanamides are reported to have similar activity to ethyl N-phenyl-S-(triphenylstannyl) isothiocarbamates (see E. J. Kupchik, M. A. Pisano, H. E. Hanke and W-C. R. Tseng, *J. Pharm. Sci.*, 67:576 (1978)). Further, triethylammonium (organocyanoamino)chlorotriphenylstannates, which are the triethylammonium chloride complexes of N-substituted N-(triphenylstannyl)cyanamides, have been found to exhibit higher antifungal activity than said cyanamides (see E. J. Kupchik, M. A. Pisano, A. M. Carroll, J. R. Lumpp, and J. A. Feiccabrino, *J. Pharm. Sci.*, 69:340 (1980)).

The antimicrobial activity of N-substituted N'-cyano-O-(triorganostannyl)isoureas and N-substituted N'-cyano-S-(triorganostannyl)isothioureas has also been reported (see E. J. Kupchik, M. A. Pisano, D. K. Parikh, and M. A. D'Amico, *J. Pharm. Sci.*, 63:261 (1974); and E. J. Kupchik, M. A. Pisano, A. V. Raghunath, R. A. Cardon, N. Formaini and C. Alleguez, *J. Pharm. Sci.*, 64:1259 (1975)).

Although all of the compounds mentioned above have also been shown to exhibit inhibitory activity toward Gram-positive bacteria, they do not exhibit effective inhibitory activity toward Gram-negative bacteria. In this respect, they resemble numerous other organotin compounds disclosed in A. K. Sijpesteijn, *Meded. Landbouwhogesch, Opzoekingsst, Staat Gent*, 24:850 (1959); A. K. Sijpesteijn, J. G. A. Luijten, and G. J. M. van der Kerk, *Fungicides, An Advanced Treatise*, D. C. Torgeson, Ed., Academic, New York, N.Y., Chap. 7 (1969); A. K. Sijpesteijn, F. Rijkens, J. G. A. Luijten, and L. C. Willemsens, *Antonie van Leeuwenhoek*, 28:346 (1962); J. G. A. Luijten, and *Organotin Compounds*, Vol. 3, A. K. Sawyer, Ed., Dekker, New York, N.Y., Chap. 12 (1972).

On the other hand, certain 5-nitro-2-substituted furans are known to inhibit both Gram-positive and Gram-negative bacteria, (see A. P. Dunlop and F. N. Peters, *The Furans*, Reinhold, New York, N.Y., p. 164 (1953); *Introduction to the Nitrofurans*, Vol. 1, Eaton Laboratories, New York, N.Y., (1958); and J. H. S. Foster and A. D. Russell, *Inhibition and Destruction of the Microbial Cell*, W. B. Hugo, Ed., Academic, New York, N.Y., Chap. 3F (1971)). However, 5-nitro-2-substituted furans do not exhibit antifungal activity. Further, some 5-nitro-2-substituted furans are not devoid of hazards, the chief of which appears to be sensitization (see A. P. Dunlp and F. N. Peters, *The Furans*, Reinhold, New York, N.Y., p. 165 (1953).

SUMMARY OF THE INVENTION

An object of the present invention is to provide organotin compounds which have fungicidal activity.

An additional object of the present invention is to provide organotin compounds which have bactericidal activity.

Another object of the present invention is to provide organotin compounds which have inhibitory activity toward Gram-positive bacteria.

Still another object of the present invention is to provide organotin compounds which have inhibitory activity toward Gram-negative bacteria.

A further object of the present invention is to provide organotin compounds which have inhibitory activity toward both Gram-positive and Gram-negative bacteria.

A still further object of the present invention is to provide organotin compounds with combined fungicidal and bactericidal activity.

Additionally, an object of the present invention is to provide fungicidal and bactericidal compositions comprising as an active ingredient, an organotin compound which degrades into a non-toxic inorganic compound and therefore into compositions which are not hazardous to the environment.

Another object of the present invention is to provide a method for inhibiting fungi and/or bacteria.

The above-described objects have been met by this invention which in one embodiment provides triorganotin 5-nitro-2-furoates represented by formula (I) below:

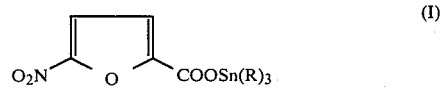

(I)

wherein R, which may be the same or different, is selected from the group consisting of an alkyl group, a cycloalkyl group, an aryl group, and an aralkyl group.

In another embodiment of this invention, the invention provides antibacterial and antifungal compositions containing an effective amount of at least one triorganotin 5-nitro-2-furoate represented by the formula (I) above, as an active ingredient.

An even further embodiment of this invention is a process for inhibiting bacterial or fungal growth.

DETAILED DESCRIPTION OF THE INVENTION

As set forth above, the present invention provides trioganotin 5-nitro-2-furoates compositions containing the same and methods of using the same, which exhibit both antifungal and antibacterial activity. It is also expected that these compounds of the invention will have miticidal and insecticidal activity.

The triorganotin 5-nitro-2-furoates of the present invention are represented by formula (I)

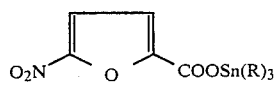
(I)

wherein R, which may be the same or different, is selected from the group consisting of an alkyl group, a cycloalkyl group, an aryl group, and an aralkyl group.

Suitable examples of alkyl groups for R include those having 1 to 8 carbon atoms such as methyl, n-propyl, n-butyl, n-octyl, etc.

Suitable examples of cycloalkyl groups for R include those having 5 to 8 carbon atoms such as cyclopentyl, cyclohexyl, cyclooctyl, etc.

Suitable examples of aryl groups for R include those having 6 to 12 carbon atoms such as phenyl, naphthyl, biphenyl, etc.

Suitable examples of aralkyl groups for R include those having 7 to 12 carbon atoms, such as benzyl, phenethyl, 2-phenyl-2,2-dimethylethyl, 6-phenyl-(n-hexyl), etc.

The triorganotin 5-nitro-2-furoate compounds wherein R is selected from the group consisting of $C_6H_5$, n—$C_4H_9$, n—$C_3H_7$, cyclo—$C_6H_{11}$ and $CH_2C(CH_3)_2C_6H_5$ are preferred with compounds wherein R is n-butyl and phenyl being particularly preferred.

The triorganotin 5-nitro-furoate compounds of the invention discussed immediately above can be prepared by reacting 5-nitro-2-furoic acid with the corresponding bis-(triorganotin) oxide as shown in Scheme I below.

Scheme I

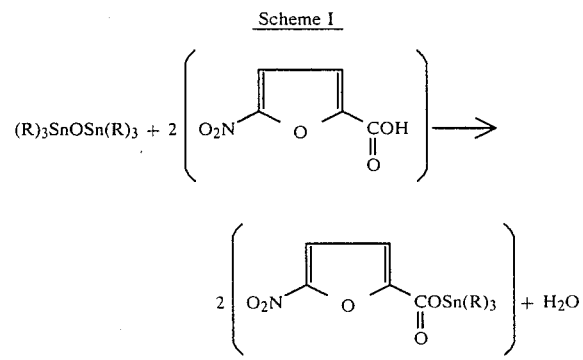

In reacting 5-nitro-2-furoic acid with the corresponding bis-(triorganotin)oxide, the reactants can be dissolved in a suitable organic solvent such as benzene and reacted at a temperature of about 80° C. for about 16 to 27 hours at a normal pressure. A suitable molar ratio of the reactants is about 2:1 of 5-nitro-2-furoic acid to the corresponding bis-(triorganotin)oxide with a suitable concentration of each reactant in the organic solvent solution being from 3% by weight to 7% by weight for 5-nitro-2-furoic acid to 11% by weight to 14% by weight for the corresponding bis(triorganotin) oxide.

Usual work-up procedures can be employed to recover the compound represented by the formula (I), e.g., filtration, and recrystallization, e.g., from benzene, heptane or heptane/benzene.

5-nitro-2-furoic acid is a known compound and can be prepared in accordance with the disclosure in Hill and White, *Am. Chem. J.*, 27:193 (1902). The corresponding bis-(triorganotin)oxides employed in the above synthesis are also known compounds and can be prepared in accordance with the disclosures in C. A. Kraus and R. H. Bullard, *J. Am. Chem. Soc.*, 51:3605 (1929); J. G. A. Luijten and G. J. M. van der Kerk, *Investigations in the Field of Organotin Chemistry,* Tin Research Institute, Greenford, Middlesex, England, 1959, pp. 107 and 111; R. K. Ingham, S. D. Rosenberg, and H. Gilman, *Chem. Rev.*, 60:459 (1960); G. J. M. van der Kerk and J. G. A. Luijten, *J. Appl. Chem.*, 6:49 (1956); E. Friebe and H. Helker, *Z. Anal. Chem.*, 192:267 (1963); H. Kriegsmann and H. Geissler, *Z. Anorg. Allgem. Chem.*, 323:170 (1963); B. G. Kushlefsky and A. Ross, *Anal. Chem.*, 34:1666 (1962); B. G. Kushlefsky, I. Simmons, and A. Ross, *Inorg. Chem.*, 2:187 (1963); N. A. Matwiyoff and R. S. Drago, *J. Organometal. Chem.*, 3:393 (1965); R. West and R. H. Baney, *J. Phys. Chem.*, 64:822 (1960); R. West, R. H. Baney, and D. L. Powell, *J. Am. Chem. Soc.*, 82:6269 (1960); and W. T. Reichle, *Inorg. Chem.*, 5:87 (1966).

The triorganotin 5-nitro-2-furoate compound of the present invention wherein R is $CH_3$ is also a particularly preferred compound and can be prepared by reacting 5-nitro-2-furoic acid with the corresponding triorganotin hydroxide as shown in Scheme II below.

Scheme II

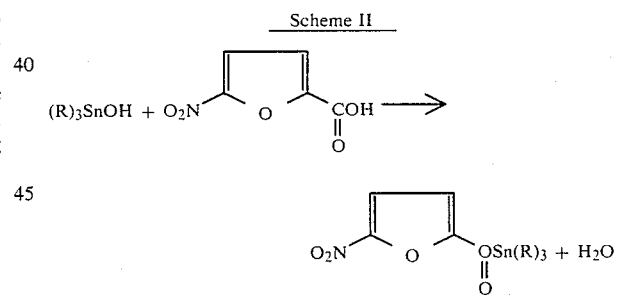

In reacting the 5-nitro-2-furoic acid with the triorganotin hydroxide, the reactants can be dissolved in a suitable organic solvent such as benzene, and reacted at a temperature of about 80° C. for about 19 hours at normal pressure. A suitable molar ratio of the reactants ranges from 1:1 of 5-nitro-2-furoic acid to the triorganotin hydroxide with a suitable concentration of each reactant in the organic solvent solution being from 12% by weight for the acid to 14% by weight for the tin compound.

Usual work-up procedures can be employed to recover the compound represented by the formula (I), e.g., filtration, and recrystallization, e.g., from benzene, heptane or heptane/benzene.

The triorganotin hydroxide employed in the above synthesis is a known compound and can be prepared in accordance with the disclosure in C. A. Kraus and R. H. Bullard, *J. Am. Chem. Soc.*, 51:3605 (1929) and J. G.

A. Luijten and G. J. M. van der Kerk, *Investigations in the Field of Organotin Chemistry*, Tin Research Institute, Greenford, Middlesex, England, 1959, p. 94.

The organotin compounds of the present invention can be solubilized in tetrahydrofuran or dimethylsulfoxide and incorporated into compositions which are useful in controlling fungi or bacteria. Examples of typical compositions are described below.

(a) miscible oils, containing for example, 5% to 20% of the active constituent, 5% to 10% of a non-ionogenic emulsifier or a mixture thereof with an anion-active emulsifier, in addition to solvents, essentially ketones such as cyclohexanone;

(b) aerosols, containing for example, acetone, methyl ethyl ketone and cyclohexanone as solvents, and methyl chloride or Freon as "propellant";

(c) wettable powders, containing for example, 50% to 80% of the active constituent in addition to wetting agents such as fat alcohol sulphates or alkylarylsulfonates, and dispersion agents and/or an inert carrier such as kaolin, chalk, pipe clay, conditioned or unconditioned with colloidal silicic acid;

(d) dusts, containing for example, 5% of the active constituent, in a mixture of kieselguhr and magnesium marlstone;

(e) seed protectors, containing for example, 50% of the active constituent in combination with kaolin and adhesives, for example spindle oil.

The compositions of the present invention are particularly useful when employed in agriculture.

The organotin compounds of the present invention can be prepared as illustrated by the following examples. Unless otherwise indicated, all parts, percents, ratios and the like are by weight.

EXAMPLE 1

Triphenyltin 5-nitro-2-furoate (Compound A) was prepared by the reaction between bis(triphenyltin)oxide (11.38 grams, 0.01589 mole) and 5-nitro-2-furoic acid (5.00 grams, 0.0318 mole) in 100 ml of benzene. The reaction mixture was refluxed for 19 hours at a temperature of 80° C. and a pressure of 1 atm. The reaction mixture was then filtered and the benzene was evaporated from the filtrate to yield 14.41 grams (90%) of crude triphenyltin 5-nitro-2-furoate, melting point 111° to 132° C. The resulting compound was recrystallized four times from a 7:5 by volume mixture of heptane to benzene to yield Compound A, melting point 111.8° to 112.5° C. The elemental analysis gave (in %) C:54.51 H:3.59 N:2.90, Sn:23.09; calculated for $C_{23}H_{17}NO_5Sn$ (in %); C:54.59 H:3.39 N:2.77, Sn:23.45.

EXAMPLE 2

Tri-n-butyltin 5-nitro-2-furoate (Compound B) was prepared by reacting bis(tri-n-butyltin)oxide (10.43 g, 0.01750 mole) with 5-nitro-2-furoic acid (5.50 g., 0.0350 mole) in 100 ml of benzene. The reaction mixture was refluxed for 19 hours at a temperature of 80° C. and a pressure of 1 atm. The reaction mixture was then filtered and the benzene was evaporated from the filtrate to yield 15.18 g (97%) of crude tri-n-butyltin 5-nitro-2-furoate, melting point 62.0°-67.0° C. The resulting compound was recrystallized four times from heptane to yield Compound B, melting point 68°-69.7° C. The elemental analysis gave (in %): C:45.6 H:6.63 N:3.28 Sn:26.67; calculated for $C_{17}H_{29}NO_5Sn$ (in %): C:45.77 H:6.55 N:3.14 Sn:26.61.

EXAMPLE 3

Tricyclohexyltin 5-nitro-2-furoate (Compound C) was prepared by reacting bis(tricyclohexyltin)oxide (11.96 g, 0.1590 mole), prepared as described in J. G. A. Luijten and G. H. M. van der Kerk, *Investigations in the Field of Organotin Chemistry*, Tin Research Institute, Greenford, Middlesex, England, p. 111 (1955), (reprinted 1959), with 5-nitro-2-furoic acid (5.00 g, 0.0318 mole) in 100 ml of benzene. The reaction mixture was refluxed for 16 hours at a temperature of 80° C. and a pressure of 1 atm. The reaction mixture was then filtered and the benzene was evaporated from the filtrate to yield 16.09 g (97%) of crude tricyclohexyltin 5-nitro-2-furoate, melting point 147°-155.5° C. The resulting compound was recrystallized four times from heptane to yield Compound C, melting point 154.8°-156° C. The elemental analysis gave (in %) C:52.92, H:6.98, N:2.82, Sn:22.57; calculated for $C_{23}H_{35}NO_5Sn$ (in %): C:52.7, H:6.73, N:2.67, Sn:22.64.

EXAMPLE 4

Tri(2-phenyl-2,2-dimethylethyl)tin 5-nitro-2-furoate (Compound D) was prepared by reacting bis(2-phenyl-2,2-dimethylethyl)tin oxide (2.63 g, 0.00250 mole), prepared as described in W. T. Reichle, *Inorg. Chem*, 5:87 (1966), with 5-nitro-2-furoic acid (0.78 g, 0.0050 mole) in 25 ml of benzene. The reaction mixture was refluxed for 26.5 hours at a temperature of 80° C. and a pressure of 1 atm. The reaction mixture was then filtered and the benzene was evaporated from the filtrate to yield 3.14 g (93%) of crude tri(2-phenyl-2,2-dimethylethyl)tin 5-nitro-2-furoate, melting point 74°-78° C. The resulting compound was then recrystallized three times from heptane to yield Compound D, melting point 79.3°-80° C. The elemental analysis gave (in %) C:62.56, H:6.26, N:2.13, Sn:17.84, calculated for $C_{35}H_{41}NO_5Sn$ (in %): C:62.33, H:6.13, N:2.08, Sn:17.60.

EXAMPLE 5

Trimethyltin 5-nitro-2-furoate (Compound E) was prepared by reacting trimethyltin hydroxide (9.20 g, 0.0509 mole) with 5-nitro-2-furoic acid (8.00 g, 0.0509 mole) in 75 ml benzene. The reaction mixture was refluxed for 19 hours at a temperature of 80° C. and a pressure of 1 atm. The resulting precipitate was collected on filter paper and dried to yield 15.30 g (94%) of crude trimethyltin 5-nitro-2-furoate, melting point 188.2°-195.5° C. The resulting compound was recrystallized three times from benzene to give Compound E, melting point 190°-192° C. The elemental analysis gave (in %) C:30.15, H:3.74, N:4.43, Sn:36.89, calculated for $C_8H_{11}NO_5Sn$ (in %): C:30.04, H:3.47, N:4.38, Sn:37.12.

The melting points in Examples 1-5 were determined with a Mel-Temp capillary melting point apparatus and are uncorrected. Further, the benzene used as a solvent in the above syntheses was dried over sodium ribbon. In addition, the water produced in the reactions was removed with the aid of a Dean-Stark trap.

The infrared spectra of the compounds produced in Examples 1-5 above were determined on a Perkin-Elmer Model 283 spectrophotometer with far infrared spectra being determined on a Perkin-Elmer Model FIS-3 spectrophotometer. The results are shown in Table I below.

TABLE I

| Compound | IR Spectra[a] | | Sn(R)₃[c] | |
|---|---|---|---|---|
| | C=O[b] | C—O | $v_{as}$ | $v_s$ |
| Compound A | 1613s | 1355s | 268s[d] | 234s |
| Compound B | 1610s | 1350s | 605w | 510w |
| Compound C | 1613s | 1353s | 610w | 510w |
| Compound D | 1613s | 1353s | 610m | 510w |
| Compound E | 1615s | 1345s | 558m | 510w |

[a]Values are expressed in centimeters$^{-1}$; S = strong, m = medium, and w = weak. The data for 4000-400 cm$^{-1}$ were obtained using potassium bromide pellets. The data for 400-200 cm$^{-1}$ were obtained using mineral oil.
[b]J. G. A. Luijten and G. J. M. van der Kerk, Rec. Trav. Chim. Pays-Bas, 82:90 (1963) and R. Okawara and M. Ohara, J. Organometal. Chem., 1:360 (1964).
[c]N. S. Dance, W. R. McWhinnie, and R. C. Poller, J. Chem. Soc, Dalton Trans., 2349 (1976) and R. C. Poller, "The Chemistry of Organotin Compounds," Academic Press, New York, N.Y., pp. 222, 227 (1970).
[d]A strong band was present at 280 cm$^{-1}$.
[e]A strong band was present at 1630 cm$^{-1}$.

BIOLOGICAL ACTIVITY

(A) Antifungal Activity

In order to determine the antifungal activity of compounds of the present invention, Compounds A to E were individually dissolved in tetrahydrofuran and 1% by weight solutions of each were sterilized by filtration (Seitz) (0.1-micrometer porosity). Dilutions of the sterile solutions were prepared and added to liquified potato dextrose agar (Difco) to yield final concentrations of 100, 10 and 1 µg/ml. The agar, containing the appropriate organotin compound, was poured into sterile petri dishes and allowed to solidify over night. The agar surface was inoculated centrally with a 2 mm² portion of the growth from a ten-day-old culture of each fungus of the group consisting of *Aspergillus niger, Chaetomium globosum, Cladosporium carpophilum, Fusarium moniliforme, Myrotheium verrucaria, Penicillium notatum, Rhizopus stolonifer, Trichoderma viride* and *Trichophyton mentagrophytes,* or from a two-day-old culture of *Saccharomyces cerevisiae.* Inoculated plates were incubated for 14 days and observations of growth inhibition were made by measuring the diameters of the colonies present on the agar surface.

A solvent was included in all evaluations, as were growth controls for all fungal species. The growth controls were employed for comparative purposes to determine the extent of growth inhibition exhibited by the organotin compounds.

The following compounds were tested for comparative purposes:

Comparative Compound 1
N—Nitrophenyl-N—(triphenylstannyl)cyanamide $$p-O_2NC_6H_4\underset{\underset{CN}{|}}{\overset{\overset{O}{\|}}{C}}NSn(C_6H_5)_3$$

Comparative Compound 2
N—Phenyl-N'—cyano-S—(triphenylstannyl)isothiourea, $$C_6H_5N=\underset{\underset{NHCN}{\|}}{C}SSn(C_6H_5)_3$$

Comparative Compound 3
N—Phenyl-N'—cyano-O—(triphenylstannyl)isourea, $$C_6H_5N=\underset{\underset{NHCN}{|}}{C}OSn(C_6H_5)_3$$

Comparative Compound 4
Ethyl N—phenyl-S—(triphenylstannyl)isothiocarbamate $$C_6H_5N=\underset{\underset{OC_2H_5}{|}}{C}SSn(C_6H_5)_3$$

Comparative Compound 5
Triethylammonium(acetylcyanoamino)chloro-triphenylstannate $$\left[ CH_3\underset{\underset{CN}{|}}{\overset{\overset{O}{\|}}{C}}NSn(C_6H_5)_3Cl \right]^- \quad [(C_2H_5)_3NH]^+$$

These compounds were tested for antifungal activity in the same manner as the triorganotin 5-nitro-2-furoates of the present invention.

The antifungal activity of the triorganotin 5-nitro-2-furoates of the present invention and the comparative compounds is set forth in Table II below.

TABLE II

| | Compounds | Aspergillus niger (ATCC 12845) | | | Chaetomium globosum (ATCC 6205) | | | Cladosporium carpophilium (ATCC 12117) | | | Fusarium moniliforme (ATCC 10052) | | | Myrothecium verrucaria (ATCC 9095) | | |
|---|---|---|---|---|---|---|---|---|---|---|---|---|---|---|---|---|
| | | 1 | 10 | 100 | 1 | 10 | 100 | 1 | 10 | 100 | 1 | 10 | 100 | 1 | 10 | 100 |
| Triorganotin 5-nitro-2-furoates | Compound A | + | 2+ | 2+ | + | + | + | 2+ | 2+ | 2+ | + | + | + | + | 2+ | 2+ |
| | Compound B | 2+ | 2+ | 2+ | 2+ | 2+ | 2+ | 2+ | 2+ | 2+ | + | 2+ | 2+ | 2+ | 2+ | 2+ |
| | Compound C | + | + | + | + | + | + | + | + | + | + | + | + | + | + | + |
| | Compound D | − | − | − | − | + | + | − | − | − | − | − | − | − | + | + |
| | Compound E | − | + | + | − | + | + | + | 2+ | 2+ | − | + | + | + | + | 2+ |
| N—nitrophenyl, N—(triphenylstannyl) cyanamide | Comparative Compound 1 | + | + | + | + | + | 2+ | + | + | + | + | + | + | + | + | + |
| N—phenyl, N'—cyano-S—(triphenylstannyl)-isothiourea | Comparative Compound 2 | − | + | 2+ | − | + | + | − | − | − | − | + | + | − | + | + |
| N—phenyl, N'—cyano-O—(triphenylstannyl)-isourea | Comparative Compound 3 | − | + | + | − | + | + | − | + | + | − | + | + | + | + | + |
| Ethyl N—phenyl-S—(triphenylstannyl)iso-thiocarbamate | Comparative Compound 4 | + | + | + | + | + | 2+ | + | + | 2+ | + | + | + | + | + | + |
| Triethylammonium-(acetylcyanoamino)-chloro-triphenyl | Comparative Compound 5 | + | + | + | + | + | + | + | + | + | + | + | + | + | + | + |

TABLE II-continued stannate

| | Compounds | Penicillium notatum (ATCC 9179) | | | Rhizopus stolonifer (ATCC 10404) | | | Saccharomyces cerevisiae (ATCC 9896) | | | Trichoderma viride (ATCC 8678) | | | Trichophyton mentagrophytes (ATCC 9129) | | |
|---|---|---|---|---|---|---|---|---|---|---|---|---|---|---|---|---|
| | | 1a | 10 | 100 | 1 | 10 | 100 | 1 | 10 | 100 | 1 | 10 | 100 | 1 | 10 | 100 |
| Triorganotin 5-nitro-2- | Compound A | + | 2+ | 2+ | + | + | + | − | + | + | + | + | + | + | 2+ | 2+ |
| furoates | Compound B | + | 2+ | 2+ | + | 2+ | 2+ | 2+ | 2+ | 2+ | 2+ | 2+ | 2+ | + | 2+ | 2+ |
| | Compound C | + | + | 2+ | − | + | + | − | − | − | + | + | + | + | + | + |
| | Compound D | − | + | + | − | − | − | − | − | − | − | − | − | + | + | + |
| | Compound E | − | + | 2+ | + | + | + | − | − | − | + | + | + | + | + | + |
| N—nitrophenyl, N—(triphenylstannyl) cyanamide | Comparative Compound 1 | + | + | + | + | + | + | − | − | + | − | + | + | + | + | 2+ |
| N—phenyl, N'—cyano-S—(triphenylstannyl) isothiourea | Comparative Compound 2 | − | + | + | − | + | 2+ | − | − | − | − | − | + | − | + | + |
| N—phenyl, N'—cyano-O—(triphenylstanntyl)-isourea | Comparative Compound 3 | − | + | + | − | + | + | − | − | 2+ | − | − | + | + | + | 2+ |
| Ethyl N—phenyl-S—(triphenylstannyl)iso-thiocarbamate | Comparative Compound 4 | + | + | + | + | + | + | − | + | + | − | + | + | + | 2+ | 2+ |
| Triethylammonium-(acetylcyanoamino) chloro-triphenyl stannate | Comparative Compound 5 | + | + | + | + | + | + | + | + | + | + | + | + | + | + | 2+ | a indicates concentrations of compound employed (μg/ml); where (−) indicates no inhibition of growth; (+) indicates partial inhibition; and (2+) indicates complete inhibition.

As indicated by the results in Table II above, Compound B exhibited the best antifungal activity of the triorganotin 5-nitro-2-furoates of the present invention. That is, Compound B completely inhibited the growth of 6 of the 10 test fungi at 1 μg/ml and all of the test fungi at 10 μg/ml.

Compound B also yielded the best antifungal activity when compared with Comparative Compounds 1–5 as demonstrated by the results in Table II above.

In addition, Compound A was the second best antifungal agent of the triorganotin 5-nitro-2-furoates of the present invention, partially inhibiting the growth of all of the test fungi, except *Saccharomyces cerevisiae*, at 1 μg/ml and completely inhibiting the growth of 5 of the 10 test fungi at 10 μg/ml.

Furthermore, Compound E of the present invention completely inhibited the growth of *Cladosporium carpophilum* at 10 μg/ml and *Penicillium notatum* at 100 μg/ml.

(B) Antibacterial Activity

The antibacterial activity of Compounds A–E was investigated by means of incorporating the compounds into sterile tryptic soy agar (Difco) at levels of 100, 10, and 1 μg/ml. The agar was also needed with a 1:100 dilution of an 18-hour old culture of the desired bacterial species in sterile distilled water. The plates were incubated for 24 hours at 37° C. with each bacterial strain. Observations of bacterial growth inhibition were made following the appropriate incubation period.

A solvent control was included in all evaluations, as were growth controls for all bacteria species. The growth controls were employed for comparative purposes to determine the extent of growth inhibition exhibited by the organotin compounds.

Comparative compounds 1–5 above were employed for comparison purposes. These compounds were tested for antibacterial activity in the same manner as the triorganotin 5-nitro-2-furoates of the present invention.

The antibacterial activity of the triorganotin 5-nitro-2-furoates of the present invention and the comparative compounds is set forth in Table III below.

TABLE III

| | | Gram-negative | | | | | | Gram-positive | | | | | | | | |
|---|---|---|---|---|---|---|---|---|---|---|---|---|---|---|---|---|
| | | Pseudomonas aeruginosa | | | Escherichia coli | | | Bacillus megaterium | | | Staphylococcus aureus | | | Bacillus subtilis | | |
| | Compounds | 1a | 10 | 100 | 1 | 10 | 100 | 1 | 10 | 100 | 1 | 10 | 100 | 1 | 10 | 100 |
| Triorganotin 5-nitro-2- | Compound A | − | − | − | − | − | − | 2+ | 2+ | 2+ | 2+ | 2+ | 2+ | | | |
| furoates | Compound B | − | + | + | − | − | 2+ | 2+ | 2+ | 2+ | 2+ | 2+ | 2+ | 2+ | 2+ | 2+ |
| | Compound C | − | − | − | − | − | − | + | 2+ | 2+ | + | 2+ | 2+ | | | |
| | Compound D | − | − | − | − | − | − | + | 2+ | 2+ | − | 2+ | 2+ | | | |
| | Compound E | − | − | 2+ | − | − | 2+ | + | + | + | − | − | + | | | |
| N—nitrophenyl, N—(triphenylstannyl) cyanamide | Comparative Compound 1 | | | | | | | | | | | | | | | |
| N—phenyl, N'—cyano-S—(triphenylstannyl)-isothiourea | Comparative Compound 2 | | | | − | − | + | | | | 2+ | 2+ | 2+ | 2+ | 2+ | 2+ |
| N—phenyl, N'—cyano-O—(triphenylstannyl)-isourea | Comparative Compound 3 | | | | − | − | − | | | | − | + | 2+ | + | 2+ | 2+ |
| Ethyl N—phenyl-S—(triphenylstannyl)iso- | Comparative Compound | | | | − | − | + | | | | 2+ | 2+ | 2+ | − | + | + |

TABLE III-continued

| | | Gram-negative | | | | | | Gram-positive | | | | | | |
| | | Pseudomonas aeruginosa | | | Escherichia coli | | | Bacillus megaterium | | | Staphylococcus aureus | | | Bacillus subtilis | | |
| Compounds | | 1a | 10 | 100 | 1 | 10 | 100 | 1 | 10 | 100 | 1 | 10 | 100 | 1 | 10 | 100 |
| thiocarbamate | 4 | | | | | | | | | | | | | | | |
| Triethylammonium-(acetylcyanoamino)chloro-triphenyl stannate | Comparative Compound 5 | | | | — | — | + | | | | 2+ | 2+ | 2+ | 2+ | 2+ | 2+ | a indicates concentration of compound employed (μg/ml); where (—)indicates no inhibition of growth; (+) indicates partial inhibition of growth; and (2+) indicates complete inhibition of growth.

All of the bacteria tested were obtained from the culture collection of the Department of Biological Sciences, St. John's University.

As demonstrated in Table III above, Compounds A and B both completely inhibited the growth of Gram-positive bacteria *Bacillus megaterium* and *Staphylococcus aureus* at the minimum concentration of 1 μg/ml. In addition, the activity of Compounds A and B towards *Staphylococcus aureus* was identical to that observed for Comparative Compounds 2, 4 and 5. Further, Comparative Compound 3 was able to completely inhibit the growth of this bacterium only at a concentration of 100 μg/ml.

Compounds B and E of the present invention also showed activity towards the Gram-negative bacteria *Pseudomonas aeruginosa* and *Escherichia coli*. That is, Compounds B and E both completely inhibited the growth of *E. coli* at 100 μg/ml whereas Comparative Compound 3 was inactive towards this bacterium at 100 μg/ml. In addition, Comparative Compounds 2, 4 and 5 inhibited the growth of *E. coli* partially only at 100 μg/ml.

The ability of Compound B to inhibit the growth of other Gram-positive bacteria, using the same test procedures as described for the antibacterial activity determined in Table III above, is illustrated in Table IV below.

TABLE IV

| Organism | Minimal Inhibition Concentration (MIC) μg/ml |
|---|---|
| Staphylococcus aureus | 0.5 |
| Micrococcus luteus | 0.05 |
| Streptococcus faecalis | 0.5 |
| Streptococcus lactis | 0.5 |
| Streptococcus salvarius | 0.5 |
| Bacillus cereus | 0.1 |
| Bacillus subtilis | 0.1 |

The ability of Compound B to inhibit another Gram-negative bacterium, using the antibacterial test procedures as described above, is illustrated in Table V below.

TABLE V

| Organism | Minimal Inhibition Concentration (MIC) μg/ml |
|---|---|
| Proteus vulgaris | 1 |

The triorganotin 2-nitro-furoates of the present invention can be applied to agricultural crops such as potatoes, tomatoes, and peaches in a method for inhibiting fungi and bacterial growth in any suitable manner such as spraying at a useful concentration of between 1 and 100 μg/ml of solution. The compounds of this invention are considered non-toxic, agriculturally safe active agents.

While this invention has been described in detail and with reference to specific embodiments thereof it would be apparent to one skilled in the art that various changes and modifications can be made therein without departing from the spirit and scope thereof.

What is claimed is:

1. A triorganotin 5-nitro-2-furoate represented by Formula (I)

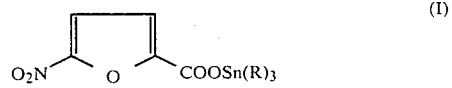

(I)

wherein R, which may be the same or different, is selected from the group consisting of an alkyl group, a cycloalkyl group containing from 5 to 8 carbon atoms, an aryl group containing from 6 to 12 carbon atoms and and aralkyl group containing from 7 to 12 carbon atoms.

2. The triorganotin 5-nitro-2-furoate of claim 1, wherein said alkyl group contains from 1 to 8 carbon atoms.

3. The triorganotin 5-nitro-2-furoate of claim 1 wherein R is $C_6H_5$, n—$C_4H_9$, n—$C_3H_7$, cyclo—$C_6H_{11}$, $CH_2C(CH_3)_2C_6H_5$ or $CH_3$.

4. The triorganotin 5-nitro-2-furoate of claim 1 wherein R is $C_6H_5$.

5. The triorganotin 5-nitro-2-furoate of claim 1 wherein R is n—$C_4H_9$.

6. The triorganotin 5-nitro-2-furoate of claim 1 wherein R is n—$C_3H_7$.

7. The triorganotin 5-nitro-2-furoate of claim 1 wherein R is $CH_3$.

8. An antifungal or antibacterial composition comprising, as an active ingredient, an antifungally or antibacterially effective amount of at least one triorganotin 5-nitro-2-furoate of claim 1 and an acceptable carrier or diluent.

9. The antifungal or antibacterial composition of claim 8, wherein R is $C_6H_5$, n—$C_3H_7$, n—$C_4H_9$, cyclo—$C_6H_{11}$, $CH_2C(CH_3)_2C_6H_5$ or $CH_3$.

10. The antifungal or antibacterial composition of claim 8, wherein R is $C_6H_5$.

11. The antifungal or antibacterial composition of claim 8, wherein R is n—$C_4H_9$.

12. The antifungal or antibacterial composition of claim 8, wherein R is n—$C_3H_7$.

13. The antifungal or antibacterial composition as in claim 8, wherein R is $CH_3$.

14. A method of inhibiting the growth of fungi comprising administering an antifungally effective amount of the triorganotin 5-nitro-2-furoate of claim 1 to the locus of said fungi.

15. The method of claim 14, wherein R is $C_6H_5$, n—$C_3H_7$, n—$C_4H_9$, cyclo—$C_6H_{11}$, $CH_2C(CH_3)_2C_6H_5$ or $CH_3$.

16. The method of claim 14, wherein R is $C_6H_5$.

17. The method of claim 14, wherein R is n—$C_3H_7$.

18. The method of claim 14, wherein R is n—$C_4H_9$.

19. The method of claim 14, wherein R is $CH_3$.

20. A method of inhibiting the growth of bacteria comprising administering an antibacterially effective amount of the triorganotin 5-nitro-2-furoate of claim 1 to the locus of said bacteria.

21. The method of claim 20, wherein R is $C_6H_5$, n—$C_3H_7$, n—$C_4H_9$, cyclo—$C_6H_{11}$, $CH_2C(CH_3)_2C_6H_5$ or $CH_3$.

22. The method of claim 20, wherein R is $C_6H_5$.

23. The method of claim 20, wherein R is n—$C_3H_7$.

24. The method of claim 20, wherein R is n-$C_4H_9$.

25. The method of claim 20, wherein R is $CH_3$.

* * * * *